United States Patent
Ikeno et al.

(10) Patent No.: US 7,205,441 B2
(45) Date of Patent: *Apr. 17, 2007

(54) METHOD FOR PRODUCING TETRAKIS (FLUOROARYL) BORATE-MAGNESIUM COMPOUND

(75) Inventors: Ikuyo Ikeno, Osaka (JP); Toshimitsu Moriguchi, Takatsuki (JP); Hitoshi Mitsui, Kitakatsuragi-gun (JP); Toshiya Iida, Sakai (JP)

(73) Assignee: Nippon Shokubai Co., Ltd., Osaka (JP)

( * ) Notice: Subject to any disclaimer, the term of this patent is extended or adjusted under 35 U.S.C. 154(b) by 318 days.

This patent is subject to a terminal disclaimer.

(21) Appl. No.: 10/431,613

(22) Filed: May 8, 2003

(65) Prior Publication Data

US 2003/0216598 A1    Nov. 20, 2003

(30) Foreign Application Priority Data

May 15, 2002 (JP) .............................. 2002-140716

(51) Int. Cl.
C07F 5/02 (2006.01)
(52) U.S. Cl. ........................................... 568/1
(58) Field of Classification Search ................ 568/1; 260/665 G
See application file for complete search history.

(56) References Cited

U.S. PATENT DOCUMENTS

| | | | | |
|---|---|---|---|---|
| 5,473,036 A | | 12/1995 | Piotrowski et al. | |
| 5,488,169 A | * | 1/1996 | Ikeda et al. | 568/3 |
| 5,693,261 A | * | 12/1997 | Krzystowczyk et al. | 260/665 G |
| 6,057,480 A | * | 5/2000 | Ueno et al. | 568/6 |
| 6,129,863 A | * | 10/2000 | Lee et al. | 260/665 G |
| 6,235,222 B1 | * | 5/2001 | Mitsui et al. | 260/665 G |
| 6,476,271 B2 | * | 11/2002 | Van Der Puy | 568/6 |

FOREIGN PATENT DOCUMENTS

| | | | |
|---|---|---|---|
| EP | 0 604 961 A2 | * | 7/1994 |
| EP | 0 838 466 | * | 10/1997 |
| EP | 838 466 A2 | | 4/1998 |
| EP | 0 995 753 A2 | * | 4/2000 |
| JP | 9-295984 | | 11/1997 |
| JP | 2000-191666 | | 7/2000 |
| WO | WO 96/27435 | | 9/1996 |
| WO | WO 00/35923 | | 6/2000 |

* cited by examiner

*Primary Examiner*—Thurman K. Page
*Assistant Examiner*—Chukwuma Nwaonicha
(74) *Attorney, Agent, or Firm*—Nixon & Vanderhye, P.C.

(57) ABSTRACT

Fluoroaryl magnesium halide is reacted with a boron compound so that a molar ratio of the fluoroaryl magnesium halide to the boron compound is not less than 3.0 and not more than 3.7, so as to produce a tetrakis (fluoroaryl) borate.magnesium compound. With this method, there occurs no hydrogen fluoride which corrodes a producing apparatus and requires troublesome waste water treatment.

8 Claims, 1 Drawing Sheet

METHOD FOR PRODUCING TETRAKIS (FLUOROARYL) BORATE-MAGNESIUM COMPOUND

FIELD OF THE INVENTION

The present invention relates to a method for producing a tetrakis (fluoroaryl) borate. magnesium compound. Further, the present invention relates to a tetrakis (fluoroaryl) borate. magnesium compound which is useful, for example, as a material for (a) a co-catalyst of a metallocene catalyst (polymerization catalyst) used in a cation complex polymerization reaction or (b) a catalyst for siloxane photopolymerization.

BACKGROUND OF THE INVENTION

Tetrakis (fluoroaryl) borate is a compound which is useful as (a) a co-catalyst of a metallocene catalyst (polymerization catalyst) used in a cation complex polymerization reaction or (b) a catalyst for siloxane photopolymerization.

A tetrakis (fluoroaryl) borate. magnesium compound is produced by reacting fluoroaryl magnesium halide with a boron compound for example. As the boron compound used in the reaction, boron trifluoride is exclusively used in industrial production due to its usability. As to a molar ratio of the fluoroaryl magnesium halide and the boron compound upon producing the tetrakis (fluoroaryl) borate. magnesium compound, Japanese Unexamined Patent Publication No. 295984/1997 (Tokukaihei 9-295984)(Publication date: Nov. 18, 1997) discloses, for example, that: fluoroaryl magnesium halide is reacted with the boron compound so that a molar ratio of the fluoroaryl magnesium halide is not less than 4.0 mol and not more than 5.0 mol with respect to 1 mol boron compound. While, Japanese Unexamined Patent Publication No. 191666/2000 (Tokukai 2000-191666)(Publication date: Jul. 11, 2000) discloses that: it is preferable to react the fluoroaryl magnesium halide with the boron compound so that a molar ratio of the fluoroaryl magnesium halide is not less than 3.5 mol and is not more than 5.0 mol with respect to 1 mol boron compound, and it is more preferable to react fluoroaryl magnesium halide with the boron compound so that a molar ratio of fluoroaryl magnesium halide is not less than 3.7 mol and is not more than 4.5 mol with respect to 1 mol boron compound.

As to the method for producing the tetrakis (fluoroaryl) borate. magnesium compound, the method using boron trifluoride as the boron compound generates not only tetrakis (fluoroaryl) borate. magnesium compound but also magnesium compound which contains fluorine atom as a by-product. Then, treating the reaction mixture with acid in order to remove the magnesium compound, hydrogen fluoride which corrodes a producing apparatus is generated. Thus, the method for producing the tetrakis (fluoroaryl) borate. magnesium compound requires a special apparatus, so that this is not preferable in industrial production.

SUMMARY OF THE INVENTION

The object of the present invention is to provide a method for producing a tetrakis (fluoroaryl) borate. magnesium compound generating no hydrogen fluoride which corrodes a producing apparatus.

In order to achieve the foregoing object, a method according to the present invention for producing a tetrakis (fluoroaryl) borate. magnesium compound represented by General Formula (1):

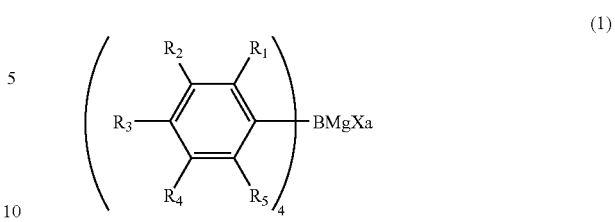

where each of $R_1$, $R_2$, $R_3$, $R_4$, and $R_5$ independently represents one of a hydrogen atom, a fluorine atom, a hydrocarbon group, and an alkoxy group, provided that at least one of $R_1$–$R_5$ represents a fluorine atom, and $X_a$ represents one of a chlorine atom, a bromine atom, and an iodine atom, includes the step of
reacting fluoroaryl magnesium halide represented by General Formula (3):

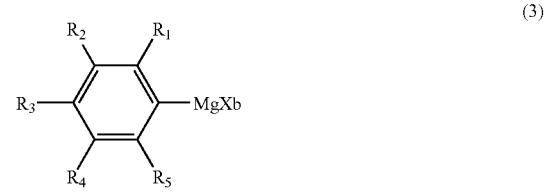

where each of $R_1$, $R_2$, $R_3$, $R_4$, and $R_5$ independently represents one of a hydrogen atom, a fluorine atom, a hydrocarbon group, and an alkoxy group, provided that at least one of $R_1$–R5 represents a fluorine atom, and $X_b$ represents one of a chlorine atom, a bromine atom, and an iodine atom, with a boron compound represented by General Formula (2)

$$B(X_c)_3 \tag{2}$$

where $X_c$ represents either a chlorine atom or a bromine atom, so that a molar ratio of the fluoroaryl magnesium halide to the boron compound is not less than 3.0 and not more than 3.7.

With the foregoing configuration, a fluorine compound is not contained as a by-product generated upon producing the tetrakis (fluoroaryl) borate. magnesium compound. Therefore, hydrogen fluoride which corrodes an apparatus is not generated upon acid treatment performed after synthesizing the tetrakis (fluoroaryl) borate. magnesium compound. Thus, it is possible to produce the tetrakis (fluoroaryl) borate. magnesium compound by using not a special apparatus but an ordinary apparatus.

For a fuller understanding of the nature and advantages of the invention, reference should be made to the ensuing detailed description taken in conjunction with the accompanying drawing.

DESCRIPTION OF THE EMBODIMENTS

Figure 1:
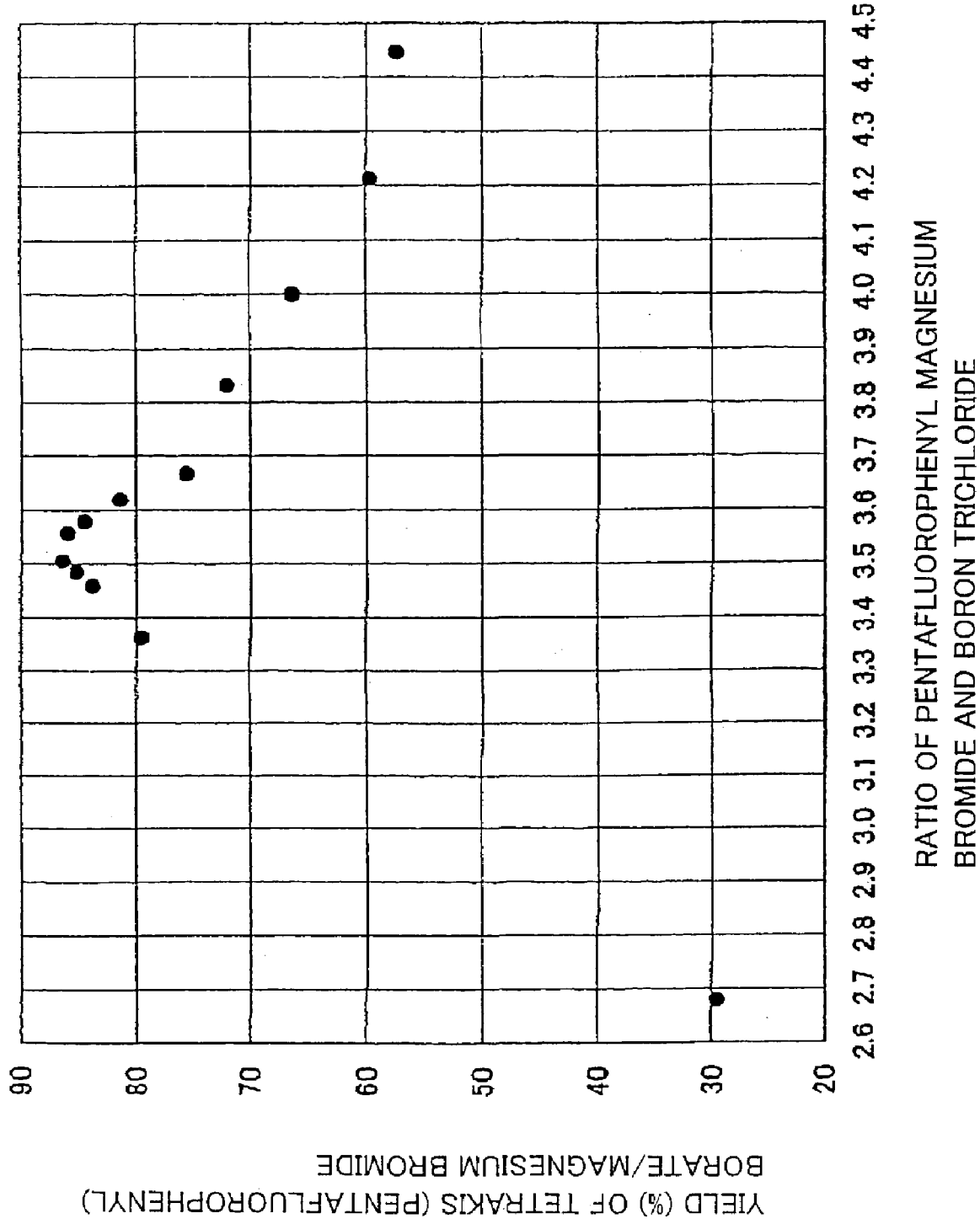
FIG. 1 is a graph showing a relationship between (a) a ratio of pentafluorophenyl magnesium bromide and boron trichloride compound and (b) a yield of tetrakis (pentafluorophenyl) borate. magnesium bromide.

One embodiment of the present invention is described as follows.

A method for producing tetrakis (fluoroaryl) borate. magnesium compound of the present invention that is represented by General Formula (1) is such that: fluoaroaryl magnesium halide represented by General Formula (3) is reacted with a boron compound so that a molar ratio of the fluoaroaryl magnesium halide is not less than 3.0 mol and not more than 3.7 mol with respect to 1 mol boron compound represented by General Formula (2). In the foregoing method, it is more preferable to use an ether as a solvent. Further, fluoroaryl magnesium halide is obtained by reacting hydrocarbon magnesium halide expressed by General Formula (4)

$$R_6MgX_b \quad (4)$$

where $R_6$ represents a hydrocarbon group, and $X_b$ represents one of a chlorine atom, a bromine atom, and an iodine atom, with fluoroarylhalide represented by General Formula (5)

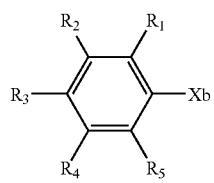

(5)

where each of $R_1$, $R_2$, $R_3$, $R_4$, and $R_5$ independently represents one of a hydrogen atom, a fluorine atom, a hydrocarbon group, and an alkoxy group, provided that at least one of $R_1$–$R_5$ represents a fluorine atom, and $X_b$ represents one of a chlorine atom, a bromine atom, and an iodine atom.

Further, for example, the fluoroaryl magnesium halide is obtained by reacting fluoroarylhalide represented by General Formula (5) with magnesium.

The tetrakis (fluoroaryl) borate. magnesium compound according to the present invention is such a compound that: each substitutional group represented by one of $R_1$–$R_5$ is independently constituted of one of a hydrogen atom, a fluorine atom, a hydrocarbon group, and an alkoxy group, provided that at least one of the substitutional groups represented by $R_1$–$R_5$ is a fluorine atom, and a substitutional group represented by $X_a$ is one of a chlorine atom, a bromine atom, and an iodine atom.

Further, the fluoroaryl magnesium halide according to the present invention is such a compound that: each substitutional group represented by one of $R_1$–$R_5$ in General Formula (3) is independently constituted of one of a hydrogen atom, a fluorine atom, a hydrocarbon group, and an alkoxy group, provided that at least one of the substitutional groups represented by $R_1$–$R_5$ is a fluorine atom, and a substitutional group represented by $X_b$ is one of a chlorine atom, a bromine atom, and an iodine atom.

Examples of the hydrocarbon group include: an aryl group such as a phenyl group; a straight or branched alkyl group containing 1 to 12 carbon atoms; a cyclic alkyl group containing 3 to 12 carbon atoms; a straight or branched alkenyl group containing 2 to 12 carbon atoms; and a cyclic alkenyl group containing 3 to 12 carbon atoms. Note that, the hydrocarbon group may further include a functional group which includes an atoms inert to the reaction in accordance with the present invention, for example, a fluorine atom, an oxygen atom, a sulfur atom, and a nitrogen atom, etc., that is, an inert functional group. Examples of the functional group specifically include a methoxy group, a methylthio group, an N,N-dimethylamino group, an o-anise group, a p-anise group, a trimethylsilyloxy group, a dimethyl-t-butylsilyloxy group, and a trifluoromethyl group.

The alkoxy group is represented by General Formula (A)

$$-OR_a \quad (A)$$

where $R_a$ represents a hydrocarbon group.

Examples of the hydrocarbon group represented by $R_a$ specifically include: an aryl group; a straight or branched alkyl group containing 1 to 12 carbon atoms; a cyclic alkyl group containing 3 to 12 carbon atoms; a straight or branched alkenyl group containing 2 to 12 carbon atoms; a cyclic alkenyl group containing 3 to 12 carbon atoms. Note that, the hydrocarbon group may further include a functional group inert to the reaction in accordance with the present invention.

Examples of the alkoxy group represented by General Formula (A) specifically include a methoxy group, an ethoxy group, an n-propoxy group, an isopropoxy group, an n-butoxy group, an isobutoxy group, a sec-butoxy group, a t-butoxy group, a cyclohexyloxy group, an allyloxy group, and a phenoxy group.

The method for producing the fluoroaryl magnesium halide according to the present invention is concretely described as follows.

Examples of the fluoroarylhalide represented by General Formula (5) specifically include chloropentafluorobenzene, bromopentafluorobenzene, iodopentafluorobenzene, 1-chloro-2,3,4,5-tetrafluorobenzene, 1-bromo-2,3,4,5-tetrafluorobenzene, 1-iodo-2,3,4,5-tetrafluorobenzene, 1-chloro-2,3,4,6-tetrafluorobenzene, 1-bromo-2,3,4,6-tetrafluorobenzene, 1-iodo-2,3,4,6-tetrafluorobenzene, 1-chloro-2,3,5,6-tetrafluorobenzene, 1-bromo-2,3,5,6-tetrafluorobenzene, 1-iodo-2,3,5,6-tetrafluorobenzene, 1-chloro-2,3,4-trifluorobenzene, 1-bromo-2,3,4-trifluorobenzene, 1-iodo-2,3,4-trifluorobenzene, 1-chloro-2,3,5-trifluorobenzene, 1-bromo-2,3,5-trifluorobenzene, 1-iodo-2,3,5-trifluorobenzene, 1-chloro-2,4,5-trifluorobenzene, 1-bromo-2,4,5-trifluorobenzene, 1-iodo-2,4,5-trifluorobenzene, 1-chloro-2,4,6-trifluorobenzene, 1-bromo-2,4,6-trifluorobenzene, 1-iodo-2,4,6-trifluorobenzene, 1-chloro-3,4,5-trifluorobenzene, 1-bromo-3,4,5-trifluorobenzene, 1-iodo-3,4,5-trifluorobenzene, 1-chloro-2,3-difluorobenzene, 1-bromo-2,3-difluorobenzene, 1-iodo-2,3-difluorobenzene, 1-chloro-2,4-difluorobenzene, 1-bromo-2,4-difluorobenzene, 1-iodo-2,4-difluorobenzene, 1-chloro-2,5-difluorobenzene, 1-bromo-2,5-difluorobenzene, 1-iodo-2,5-difluorobenzene, 1-chloro-2,6-difluorobenzene, 1-bromo-2,6-difluorobenzene, 1-iodo-2,6-difluorobenzene, 1-chloro-3,4-difluorobenzene, 1-bromo-3,4-difluorobenzene, 1-iodo-3,4-difluorobenzene, 1-chloro-3,5-difluorobenzene, 1-bromo-3,5-difluorobenzene, 1-iodo-3,5-difluorobenzene, 1-chloro-2-fluorobenzene, 1-bromo-2-fluorobenzene, 1-iodo-2-fluorobenzene, 1-chloro-3-fluorobenzene, 1-bromo-3-fluorobenzene, 1-iodo-3-fluorobenzene, 1-chloro-4-fluorobenzene, 1-bromo-4-fluorobenzene, and 1-iodo-4-fluorobenzene.

Examples of the hydrocarbon magnesium halide represented by General Formula (4) specifically include phenyl magnesium chloride, phenyl magnesium bromide, phenyl magnesium iodide, methyl magnesium chloride, methyl magnesium bromide, methyl magnesium iodide, ethyl magnesium chloride, ethyl magnesium bromide, ethyl magnesium iodide, n-propyl magnesium chloride, n-propyl magnesium bromide, n-propyl magnesium iodide, isopropyl magnesium chloride, isopropyl magnesium bromide, isopropyl magnesium iodide, n-butyl magnesium chloride, n-butyl magnesium bromide, n-butyl magnesium iodide, allyl magnesium chloride, allyl magnesium bromide, allyl magnesium iodide, cyclohexyl magnesium chloride, cyclohexyl magnesium bromide, and cyclohexyl magnesium iodide.

It is preferable that a molar ratio of the hydrocarbon magnesium halide to the fluoroarylhalide is not less than 0.8 and not more than 2.0, and it is more preferable that the molar ratio is not less than 0.9 and not more than 1.5, and it is specifically preferable that the molar ratio is not less than 0.9 and not more than 1.2. In case the molar ratio is less than 0.8, a yield of the tetrakis (fluoroaryl) borate. magnesium compound which is a final product may be reduced. Further, in case the molar ratio is more than 2.0, an amount of the hydrocarbon magnesium halide which has not reacted may be increased. Thus, for example, there occurs a trouble to remove the compounds that have not reacted. Therefore, generally, it is preferable to perform the reaction so that the molar ratio of the hydrocarbon magnesium halide to the fluoroarylhalide is not less than 0.9 and not more than 1.2 so as not to leave the fluoroarylhalide that has not reacted and so as to use the hydrocarbon magnesium halide that has not reacted, in the next step, without removing the hydrocarbon magnesium halide.

The reaction of fluoroarylhalide and the hydrocarbon magnesium halide are carried out in an ether solvent, more preferably, in a solvent containing a chain ether solvent. The solvent containing the chain ether solvent is a liquid compound which can make the fluoroarylhalide and the hydrocarbon magnesium halide dissolve or suspend, and is inert to the reaction in according with the present invention.

Examples of the ether solvent specifically include an aliphatic ether solvent such as diethyl ether, dipropyl ether, diisopropyl ether, dibutyl ether, t-butylmethyl ether, diisoamyl ether, 1,2-dimethoxyethane, 1,2-diethoxyethane, cyclopenthyl methyl ether, cyclohexyl methyl ether, cyclopenthyl ethyl ether, and cyclohexyl ethyl ether. Only one kind of them may be used, or two or more kinds of them may be used in combination.

Further, the ether solvent exemplified above may be mixed with a solvent other than the chain ether solvent, for example, the ether solvent may be mixed with: an aliphatic hydrocarbon solvent such as pentane, hexane, and heptane; an alicyclic hydrocarbon solvent such as cyclopentane, cyclohexane, and methylcyclohexane; an aromatic hydrocarbon solvent such as benzene, toluene, xylene, and anisole; and the like, so as to be used as a mixed solution. Further, also an appropriate amount of cyclic ether such as tetrahydrofuran can be mixed so long as ring-opening polymerization does not occur. Only one kind of solvent mixed with the chain ether solvent may be used as required, or two ore more kinds may be used in combination.

A rate at which the ether solvent is contained in the solvent (concentration) is set so that it is possible to smoothly promote the reaction, but it is preferable that the rate is not less than 1.0 wt %, and it is more preferable that the rate is not less than 5.0 wt %, and it is specifically preferable that the rate is not less than 10.0 wt %. When the rate is less than 1.0 wt %, a reaction rate may be extremely slow.

A using amount of solvent is set so that it is possible to make the fluoroarylhalide and the hydrocarbon magnesium halide dissolve or suspend and it is possible to smoothly promote the reaction, and it is preferable that concentration of the synthesized fluoroaryl magnesium halide contained in the reaction solution is not less than 0.1 wt % and not more than 80 wt %, and it is more preferable that the concentration is not less than 1.0 wt % and not more than 70 wt %, and it is specifically preferable that the concentration is not less than 5.0 wt % and not more than 60 wt %. When the concentration is less than 0.1 wt %, more solvent is required, so that a reaction efficiency drops, and a reaction rate may be extremely slow. Further, when the concentration is more than 80 wt %, it may be difficult to treat the reaction mixture, for example, the fluoroaryl magnesium halide is deposited.

Examples of a process for mixing fluoroarylhalide with the hydrocarbon magnesium halide are as follows: solution of the hydrocarbon magnesium halide may be dropped into fluoroarylhalide or solution thereof; or the fluoroarylhalide or the solution thereof may be dropped into the solution of hydrocarbon magnesium halide; further, (a) the fluoroarylhalide or the solution thereof and (b) the solution of hydrocarbon magnesium halide may be dropped into the solvent.

A temperature upon the reaction is not specifically limited, but it is preferable that the temperature is not less than $-30°$ C. and not more than a reflux temperature of the solvent, and it is more preferable that the temperature is not less than $-20°$ C. and not more than a lower one of $200°$ C. and a reflux temperature of the solvent, and it is specifically preferable that the temperature is not less than $-10°$ C. and not more than a lower one of $100°$ C. and the reflux temperature of the solvent.

Further, the reaction rate and a pressure upon the reaction are not specifically limited, but are set according to other reaction conditions such as a reaction temperature, an amount of the hydrocarbon magnesium halide, an amount of the fluoroarylhalide, a combination of the both, and composition of the solvent, as required, so as to complete the reaction. Thus, a pressure may be applied at an ordinary pressure, or an increased pressure, or a reduced pressure. Further, it is preferable that the reaction is performed under an atmosphere of inert gas such as nitrogen gas.

By performing the Grignard exchange reaction, fluoroaryl magnesium halide represented by General Formula (3) is produced.

Next, a method according to the present invention for producing a tetrakis (fluoroaryl) borate. magnesium compound is concretely described as follows.

Examples of the boron compound represented by General Formula (2) include boron trichloride, boron tribromide, and the like. The boron compound may constitute a complex with diethyl ether, tetrahydrofuran, and the like for example. It is preferable that a molar ratio of the fluoroaryl magnesium halide represented by General Formula (3) to the boron compound (fluoroaryl magnesium halide/boron compound) is not less than 3.0 and 3.7, and it is more preferable that the molar ratio is not less than 3.0 and 3.6, and it is still more preferable that the molar ratio is not less than 3.3 and 3.6, and it is most preferable that the molar ratio is not less than 3.4 and 3.6.

By adjusting the molar ratio so as to be in a specific range, it is possible to improve a yield of the obtained tetrakis (fluoroaryl) borate. magnesium compound based on the fluoroarylhalide used as a raw material for the compound.

The reaction of the fluoroaryl magnesium halide and the boron compound is performed by mixing (a) the fluoroaryl magnesium halide solution (reaction solution) obtained by synthesizing the fluoroaryl magnesium halide with (b) the boron compound or solution thereof.

A using amount of the solvent is set so that it is possible to make the fluoroaryl magnesium halide and the boron compound dissolve or suspend and it is possible to smoothly promote the reaction. Further, in case of mixing the boron compound as a solution for example, a solvent used to produce the solution may be the same compound as the solvent used to produce the fluoroaryl magnesium halide, or may be a different compound. Further, it is also possible to dilute the reaction solution by adding the solvent as required, or it is also possible to perform solvent exchange by distilling off the solvent used upon the reaction.

The process for mixing the fluoroaryl magnesium halide solution with the boron compound may be such that: the boron compound or solution thereof is dropped into the solution of fluoroaryl magnesium halide, the solution of fluoroaryl magnesium halide is dropped into the boron compound or solution thereof, or the fluoroaryl magnesium halide solution and the boron compound or solution thereof are dropped into the solvent.

It is more preferable that a mixing temperature upon mixing the solution of fluoroaryl magnesium halide with the boron compound is not less than −30° C. and not more than a reflux temperature of the solvent, and it is still more preferable that the mixing temperature is not less than −20° C. and not more than a lower one of 200° C. and the reflux temperature of the solvent, and it is specifically preferable that the mixing temperature is not less than −10° C. and not more than a lower one of 150° C. and the reflux temperature of the solvent.

Further, it is more preferable that a reaction temperature upon the reaction is not less than 0° C. and not more than a lower one of 200° C. and the reflux temperature of the solvent, and it is specifically preferable that the reaction temperature is not less than 30° C. and not more than a lower one of 150° C. and the reflux temperature of the solvent. When the reaction temperature is lower than −30° C., the reaction rate may be extremely reduced, and when the reaction temperature is higher than 200° C., the tetrakis (fluoroaryl) borate. magnesium compound may be decomposed.

Further, the reaction rate and a pressure upon the reaction are not specifically limited, but are set according to other reaction conditions such as a reaction temperature, an amount of fluoroaryl magnesium halide, an amount of the boron compound, a combination of the both, and composition of the solvent, as required, so as to complete the reaction. Thus, a pressure may be applied at an ordinary pressure, or an increased pressure, or a reduced pressure. Further, it is preferable that the reaction is performed under an atmosphere of inert gas such as nitrogen gas. Note that, it is also possible to distill off the solvent and/or alkyl halide which is produced as a by-product in the process of producing the fluoroaryl magnesium halide, when or after the reaction is performed. Alternately, it is also possible to perform the solvent exchange when or after the reaction is performed.

By performing the reaction, it is possible to produce the tetrakis (fluoroaryl) borate. magnesium compound represented by General Formula (1). Further, by performing acid treatment with respect to the tetrakis (fluoroaryl) borate. magnesium compound, it is possible to obtain tetrakis (fluoroaryl) borate hydrogen. A by-product generated by the acid treatment performed with respect to the tetrakis (fluoroaryl) borate. magnesium compound is a chloric compound or a bromic compound. Thus, a by-product containing no fluorine is generated.

According to the method for producing the tetrakis (fluoroaryl) borate. magnesium compound, there occurs no hydrogen fluoride upon the acid treatment performed with respect to the tetrakis (fluoroaryl) borate. magnesium compound, so that a producing apparatus is not corroded. Thus, in the foregoing producing method, it is possible to produce the tetrakis (fluoroaryl) borate. magnesium compound by means of not a special apparatus but an ordinary apparatus.

The following Examples and Comparative Example will further detail the present invention, but the present invention is not limited by the description thereof.

EXAMPLE 1

Air inside a reaction vessel equipped with a thermometer, a dropping funnel, a stirrer, a nitrogen gas conduit, and a reflux condenser was replaced with a nitrogen gas in a satisfactory manner. Then, 180 ml of a dibutyl ether solution containing 0.355 mol of ethylmagnesium bromide as the hydrocarbon magnesium halide was charged to the reaction vessel. Further, 0.366 mol of bromopentafluorobenzene as the fluoroarylhalide was charged to the dropping funnel.

Next, after dropping bromopentafluorobenzene in the dropping funnel over 120 minutes at 25° C., the content of the reaction vessel was stirred for 30 minutes at 25° C., so as to obtain pentafluorophenyl magnesium bromide as the fluoroaryl magnesium halide, obtained as a colorless dibutyl ether.

The yield of the pentafluorophenyl magnesium bromide generated in the reaction was calculated by measuring a $^{19}$F-NMR (magnetic nuclear resonance) spectrum. That is, the $^{19}$F-NMR was measured under a usual condition using p-fluorotoluene as an internal standard reference. In the measurement, trifluoroacetic acid was used as a reference material, and the signal of the reference material was set at 0 ppm. An integral value of a fluorine atom of the p-fluorotoluene and an integral value of a fluorine atom of an ortho position of a pentafluorophenyl group of the pentafluorophenyl magnesium bromide were given from the obtained $^{19}$F-NMR chart, and the amount of the pentafluorophenyl magnesium bromide was calculated from these integral values. As a result, the yield of the pentafluorophenyl magnesium bromide was 99.4% based on the bromopentafluorobenzene.

Next, 80 ml of hexane solution containing 0.104 mol of boron trichloride was charged to the dropping funnel of the reaction vessel containing the dibutyl ether solution of the pentafluorophenyl magnesium bromide. Next, after dropping the hexane solution of boron trichloride in the dropping funnel over 120 minutes at 25° C., the reaction mixture was heated to 100° C. for two hours while distilling off hexane and ethyl bromide generated as a by-product upon synthesizing the pentafluorophenyl magnesium bromide at an ordinary pressure, and were stirred for three hours at 100° C., thereby obtaining tetrakis (pentafluorophenyl) borate. magnesium bromide as a white suspension. As a result of analysis by a high-performance liquid chromatography, the yield of the tetrakis (pentafluorophenyl) borate. magnesium bromide was 86.4% based on the bromopentafluorobenzene.

EXAMPLE 2

Air inside the reaction vessel as in Example 1 was replaced with a nitrogen gas in a satisfactory manner. Then, 180 ml of dibutyl ether solution containing 0.354 mol of ethyl magnesium bromide as hydrocarbon magnesium halide was charged to the reaction vessel. Further, 0.365 mol of bromopentafluorobenzene was charged to the dropping funnel as fluoroarylhalide. Next, after dropping the bromopentafluorobenzene in the dropping funnel over 120 minutes at 25° C., the content of the reaction vessel was stirred for thirty minutes at 25° C., thereby obtaining pentafluorophenyl magnesium bromide as the fluoroaryl magnesium halide, obtained as a colorless dibutyl ether solution.

As a result of analysis performed as in Example 1, the yield of the pentafluorophenyl magnesium bromide was 99.3% based on the bromopentafluorobenzene.

Next, 80 ml of hexane solution containing 0.105 mol of boron trichloride was charged to the dropping funnel of the reaction vessel containing the dibutyl ether solution of the pentafluorophenyl magnesium bromide. Next, after dropping the hexane solution of boron trichloride in the dropping funnel over 120 minutes at a room temperature, the reaction mixture was heated to 100° C. for two hours while distilling off hexane and ethyl bromide generated as a by-product upon synthesizing the pentafluorophenyl magnesium bromide at an ordinary pressure, and were stirred for three hours at 100° C., thereby obtaining tetrakis (pentafluorophenyl) borate. magnesium bromide as a white suspension. As a result of analysis by a high-performance liquid chromatography, the yield of the tetrakis (pentafluorophenyl) borate. magnesium bromide was 82.7% based on the bromopentafluorobenzene.

EXAMPLE 3

Air inside the reaction vessel as in Example 1 was replaced with a nitrogen gas in a satisfactory manner. Then, 180 ml of dibutyl ether solution containing 0.356 mol of pentafluorophenyl magnesium bromide as fluoroaryl magnesium halide was charged to the reaction vessel. Further, 76 ml of hexane solution containing 0.0982 mol of boron trichloride was charged to the dropping funnel. Next, after dropping the hexane solution of boron trichloride over 120 minutes at 25° C., the reaction mixture was heated to 100° C. for two hours while distilling off hexane at an ordinary pressure, and was stirred for three hours at 100° C., thereby obtaining tetrakis (pentafluorophenyl) borate. magnesium bromide as a white suspension. As a result of analysis by a high-performance liquid chromatography, the yield of the tetrakis (pentafluorophenyl) borate. magnesium bromide was 83.8% based on the pentafluphenyl magnesium bromide.

EXAMPLE 4

The same reaction as in Example 1 was performed except that an amount of the boron trichloride is changed with respect to the pentafluorophenyl magnesium bromide. As a result, tetrakis (pentafluorophenyl) borate. magnesium bromide was obtained. The yields of the tetrakis (pentafluorophenyl) borate. magnesium bromide were calculated based on the bromopentafluorobenzene, and thus calculated results are shown together in FIG. 1 as a graph.

COMPARATIVE EXAMPLE 1

Air inside the reaction vessel as in Example 1 was replaced with a nitrogen gas in a satisfactory manner. Then, 360 ml of dibutyl ether solution containing 0.707 mol of ethyl magnesium bromide as the hydrocarbon magnesium halide was charged to the reaction vessel. Further, 0.729 mol of bromopentafluorobenzene as the fluoroaryl halide was charged to the dropping funnel. Next, after dropping bromopentafluorobenzene in the dropping funnel over 120 minutes at 25° C., the reaction mixture was stirred for thirty minutes at 25° C., thereby obtaining pentafluorophenyl magnesium bromide as the fluoroaryl magnesium halide, as a colorless dibutyl ether solution.

As a result of analysis performed as in Example 1, the yield of bromopentafluorobenzene was 99.1% based on pentafluphenyl magnesium bromide.

Next, 160 ml of hexane solution containing 0.175 mol of boron trichloride was charged to the dropping funnel of the reaction vessel containing the dibutyl ether solution of the pentafluorophenyl magnesium bromide. Next, after dropping the hexane solution of boron trichloride contained in the dropping funnel over 120 minutes at 25° C., the reaction mixture was heated to 100° C. for two hours while distilling off hexane and ethyl bromide generated as a by-product upon synthesizing the pentafluorophenyl magnesium bromide at an ordinary pressure, and were stirred for three hours at 100° C., thereby obtaining tetrakis (pentafluorophenyl) borate. magnesium bromide as a white suspension.

As a result of analysis by a high-performance liquid chromatography, the yield of the tetrakis (pentafluorophenyl) borate. magnesium bromide was 66.3% based on the bromopentafluorobenzene. Thus, a molar ratio of boron trichloride to pentafluorophenyl magnesium bromide deviates from a preferable range of the present invention, so that the yield of the tetrakis (pentafluorophenyl) borate. magnesium bromide is reduced.

COMPARATIVE EXAMPLE 2

Air inside the reaction vessel as in Example 1 was replaced with a nitrogen gas in a satisfactory manner. Then, 180 ml of dibutyl ether solution containing 0.356 mol of pentafluorophenyl magnesium bromide as the fluoroaryl magnesium halide was charged to the reaction vessel. Further, 105 ml of hexane solution containing 0.135 mol of boron trichloride was charged to the dropping funnel. Next, after dropping the hexane solution of the boron trichloride over 135 minutes at 25° C., the reaction mixture was heated to 100° C. for 82 minutes while distilling off the hexane at an ordinary temperature, and was stirred for three hours at 100° C., thereby obtaining tetrakis (pentafluorophenyl) borate. magnesium bromide as an yellow suspension.

As a result of analysis by a high-performance liquid chromatography, the yield of the tetrakis (pentafluorophenyl) borate. magnesium bromide was 29.6% based on the bromopentafluorobenzene. Thus, a molar ratio of boron trichloride to pentafluorophenyl magnesium bromide deviates from a preferable range of the present invention, so that the yield of the tetrakis (pentafluorophenyl) borate. magnesium bromide is reduced.

The invention being thus described, it will be obvious that the same may be varied in many ways. Such variations are not to be regarded as a departure from the spirit and scope of the invention, and all such modifications as would be obvious to one skilled in the art intended to be included within the scope of the following claims.

What is claimed is:

1. A method for producing a tetrakis (fluoroaryl) borate-magnesium halide compound represented by Formula (1):

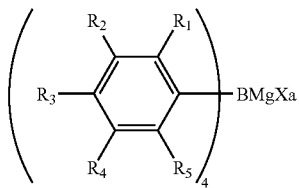

where each of $R_1$, $R_2$, $R_3$, $R_4$, and $R_5$ independently represents one of a hydrogen atom, a fluorine atom, a hydrocarbon group, and an alkoxy group, provided that at least one of $R_1$–$R_5$ represents a fluorine atom, and $X_a$ represents one of a chlorine atom, a bromine atom, and an iodine atom, comprising the step of reacting fluoroaryl magnesium halide represented by Formula (3):

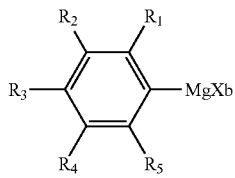

where each of $R_1$, $R_2$, $R_3$, $R_4$, and $R_5$ independently represents one of a hydrogen atom, a fluorine atom, a hydrocarbon group, and an alkoxy group, provided that at least one of $R_1$–$R_5$ represents a fluorine atom, and $X_b$ represents one of a chlorine atom, a bromine atom, and an iodine atom, with a boron compound represented by Formula (2)

$$B(X_c)_3 \tag{2}$$

where $X_c$ represents either a chlorine atom or a bromine atom, so that a molar ratio of the fluoroaryl magnesium halide to the boron compound is not less than 3.0 and not more than 3.7.

2. The method as set forth in claim 1, wherein an ether solvent is used.

3. The method as set forth in claim 1, wherein:

said fluoraryl magnesium halide is obtained by reacting hydrocarbon magnesium halide represented by Formula (4)

$$R_6MgX_b \tag{4}$$

where $R_6$ represents a hydrocarbon group, and $X_b$ represents one of a chlorine atom, a bromine atom, and an iodine atom, in an ether solvent with fluoroarylhalide represented by Formula (5):

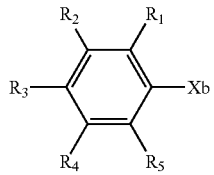

where each of $R_1$, $R_2$, $R_3$, $R_4$, and $R_5$ independently represents one of a hydrogen atom, a fluorine atom, a hydrocarbon group, and an alkoxy group, provided that at least one of $R_1$–$R_5$ represents a fluorine atom, and $X_b$ represents one of a chlorine atom, a bromine atom, and an iodine atom.

4. The method as set forth in claim 3, wherein a molar ratio of the hydrocarbon magnesium halide to the fluoroarylhalide is not less than 0.8 and not more than 2.0.

5. The method as set forth in claim 3, wherein the hydrocarbon magnesium halide represented by Formula (4) is any one of phenyl magnesium chloride, phenyl magnesium bromide, phenyl magnesium iodide, methyl magnesium chloride, methyl magnesium bromide, methyl magnesium iodide, ethyl magnesium chloride, ethyl magnesium bromide, ethyl magnesium iodide, n-propyl magnesium chloride, n-propyl magnesium bromide, n-propyl magnesium iodide, isopropyl magnesium chloride, isopropyl magnesium bromide, isopropyl magnesium iodide, n-butyl magnesium chloride, n-butyl magnesium bromide, n-butyl magnesium iodide, allyl magnesium chloride, allyl magnesium bromide, allyl magnesium iodide, cyclohexyl magnesium chloride, cyclohexyl magnesium bromide, and cyclohexyl magnesium iodide.

6. The method as set forth in claim 3, wherein the fluoroarylhalide represented by Formula (5) is any one of chloropentafluorobenzene, bromopentafluorobenzene, iodopentafluorobenzene, 1-chloro-2,3,4,5-tetrafluorobenzene, 1-bromo-2,3,4,5-tetrafluorobenzene, 1-iodo-2,3,4,5-tetrafluorobenzene, 1-chloro-2,3,4,6-tetrafluorobenzene, 1-bromo-2,3,4,6-tetrafluorobenzene, 1-iodo-2,3,4,6-tetrafluorobenzene, 1-chloro-2,3,5,6-tetrafluorobenzene, 1-bromo-2,3,5,6-tetrafluorobenzene, 1-iodo-2,3,5,6-tetrafluorobenzene, 1-chloro-2,3,4-trifluorobenzene, 1-bromo-2,3,4-trifluorobenzene, 1-iodo-2,3,4-trifluorobenzene, 1-chloro-2,3,5-trifluorobenzene, 1-bromo-2,3,5-trifluorobenzene, 1-iodo-2,3,5-trifluorobenzene, 1-chloro-2,4,5-trifluorobenzene, 1-bromo-2,4,5-trifluorobenzene, 1-iodo-2,4,5-trifluorobenzene, 1-chloro-2,4,6-trifluorobenzene, 1-bromo-2,4,6trifluorobenzene, 1-iodo-2,4,6-trifluorobenzene, 1-chloro-3,4,5-trifluorobenzene, 1-bromo-3,4,5-trifluorobenzene, 1-iodo-3,4,5-trifluorobenzene, 1-chloro-2,3-difluorobenzene, 1-bromo-2,3-difluorobenzene, 1-iodo-2,3-difluorobenzene, 1-chloro-2,4-difluorobenzene, 1-bromo-2,4-difluorobenzene, 1-iodo-2,4-difluorobenzene, 1-chloro-2,5-difluorobenzene, 1-bromo-2,5-difluorobenzene, 1-iodo-2,5-difluorobenzene, 1-chloro-2,6-difluorobenzene, 1-bromo-2,6-difluorobenzene, 1-iodo-2,6-difluorobenzene, 1-chloro-3,4-difluorobenzene, 1-bromo-3,4-difluorobenzene, 1-iodo-3,4-difluorobenzene, 1-chloro-3,5-difluorobenzene, 1-bromo-3,5-difluorobenzene, 1-iodo-3,5-difluorobenzene, 1-chloro-2-fluorobenzene, 1-bromo-2-fluorobenzene, 1-iodo-2-fluorobenzene, 1-chloro-3-fluorobenzene, 1-bromo-3-fluorobenzene, 1-iodo-3-fluorobenzene, 1-chloro-4-fluorobenzene, 1-bromo-4-fluorobenzene, and 1-iodo-4-fluorobenzene.

7. The method as set forth in claim 3, wherein the ether solvent is any one of diethyl ether, dipropyl ether, diisopropyl ether, dibutyl ether, t-butyl methyl ether, diisoamyl ether, cyclopenthyl methyl ether, cyclohexyl methyl ether, 1,2-dimethoxyethane, and 1,2-diethoxyethane.

8. The method as set forth in claim 3, wherein the fluoroarylhalide represented by Formula (5) is any one of chloropentafluorobenzene, bromopentafluorobenzene, and iodopentafluorobenzene.

* * * * *